United States Patent
Mayer

[11] Patent Number: 6,113,867
[45] Date of Patent: Sep. 5, 2000

[54] COMPACT CASSETTE FOR DENTAL INSTRUMENTS

[75] Inventor: Stanley E. Mayer, Middle Town, N.Y.

[73] Assignee: Coltene/Whaledent, Inc., Mahwah, N.J.

[21] Appl. No.: 09/181,963

[22] Filed: Oct. 29, 1998

[51] Int. Cl.[7] ................. A61L 2/07; A61B 19/02
[52] U.S. Cl. ............ 422/300; 422/297; 206/369; 206/370; 206/438
[58] Field of Search ............ 422/28, 292, 297, 422/300; 206/205, 207, 210, 305, 363, 370, 438, 439

[56] References Cited

U.S. PATENT DOCUMENTS

| | | | |
|---|---|---|---|
| 4,748,993 | 6/1988 | Llewellyn | 422/300 |
| 4,762,688 | 8/1988 | Berry, Jr. | |
| 4,774,063 | 9/1988 | Runnells | |
| 4,928,917 | 5/1990 | Wolf | 422/300 |
| 4,959,199 | 9/1990 | Brewer | |
| 5,084,251 | 1/1992 | Thomas | |
| 5,215,726 | 6/1993 | Kudla, et al. | |
| 5,433,929 | 7/1995 | Riihimaki, et al. | |
| 5,433,930 | 7/1995 | Taschner | 422/300 |
| 5,451,379 | 9/1995 | Bowlin, Jr. | |
| 5,505,916 | 4/1996 | Berry, Jr. | 422/300 |
| 5,573,741 | 11/1996 | Riley | |
| 5,840,261 | 11/1998 | Monch | 422/300 |

*Primary Examiner*—Elizabeth McKane
*Attorney, Agent, or Firm*—Helfgott & Karas, PC.

[57] ABSTRACT

A tray having a pair of stamped instrument racks includes a pair of side walls which taper transversely and longitudinally toward each other at their opposite ends. The tapered ends form wedge-like extensions which lead into a pair of rounded end walls. The tapered ends and rounded end walls form a chisel shaped profile which facilitates insertion of the tray into an autoclave bag. A spring-actuated retainer is operable with one hand to secure or release a plurality of instruments held in the racks.

16 Claims, 4 Drawing Sheets

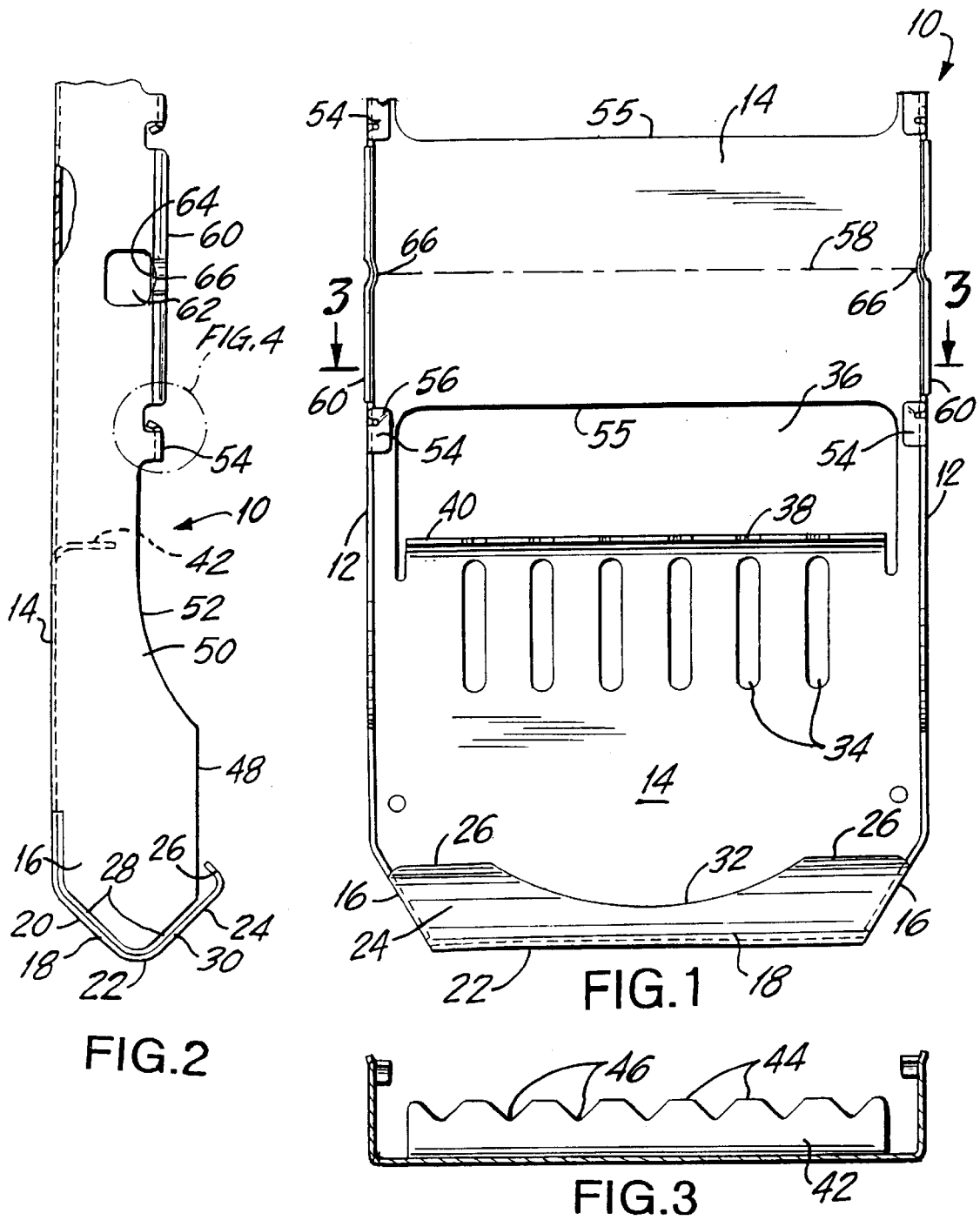

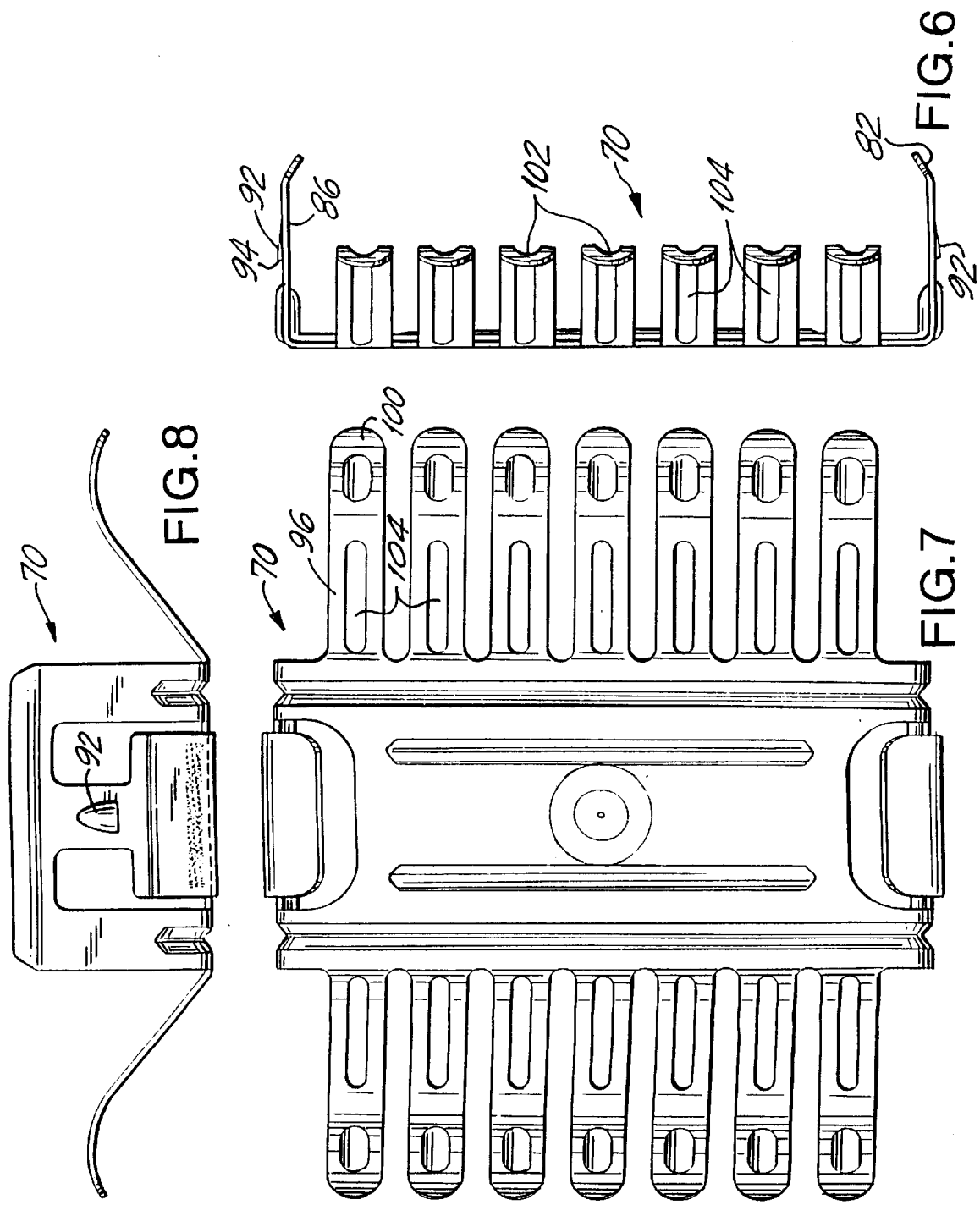

COMPACT CASSETTE FOR DENTAL INSTRUMENTS

BACKGROUND OF THE INVENTION

1. Field of the Invention

The present invention relates in general to a tray and retainer for holding medical instruments and in particular to a safe, compact dental cassette adapted for use with compact autoclaves and compact sterilization pouches known as autoclave bags.

2. Description of Prior Developments

Medical instruments, and particularly dental instruments, can be placed in a tray or similar holder before and after use on a patient. After use, the tray, along with the instruments, is subsequently placed in an ultrasonic cleaner to remove debris from the instruments. After ultrasonic cleaning, the instruments may be wrapped in a protective material and then heated in an autoclave to sterilize the instruments in preparation for the next patient use.

In some cases, the trays carrying the instruments cannot fit within the autoclave. This necessitates either eliminating the use of the tray or removing the instruments from the tray, placing the loose instruments in an autoclave bag and then placing the autoclave bag in an autoclave. As the instruments are not sterile when being bagged, the dental technician placing the instruments in the bag is placed at risk of contamination and infection by contact with the instruments. After sterilization, the instruments must be individually removed from autoclave bag. This individual removal can result in contamination of the instruments and is generally considered inconvenient. Moreover, the loose instruments can impact one another in the autoclave bag and result in the dulling of sharp instruments.

Accordingly, what is needed is a compact cassette for securely holding medical and dental instruments in both compact autoclave bags as well as compact autoclaves.

A further need exists for such a cassette and which can fit within virtually all sterilization autoclaves so that instruments need not be removed from the cassette during autoclaving.

A further need exists for a compact cassette which facilitates placement within autoclave bags and particularly within compact autoclave bags.

Another need exists for a compact cassette particularly adapted for use with compact autoclaves and which can be easily fitted within a compact autoclave bag.

Still another need exists for a compact cassette which can securely hold one or more instruments in place during ultrasonic cleaning, autoclaving, and subsequent removal from an autoclave bag.

Yet another need exists for such a cassette having an instrument retainer which can be installed and removed with one hand thereby leaving a dentist or doctor free to use the other hand as needed.

SUMMARY OF THE INVENTION

The present invention has been developed to fulfil the needs noted above and therefore has as an object the provision of a compact cassette for securely holding medical and dental instruments in place during medical and dental procedures, ultrasonic cleaning, insertion within an autoclave bag, autoclaving and removal from an autoclave bag.

Another object of the invention is the provision of a compact cassette for holding medical and dental instruments and which is particularly adapted and constructed to facilitate its insertion into and removal from a compact autoclave bag.

Yet another object of the invention is the provision of a compact cassette for holding medical and dental instruments and which can be placed within virtually all sterilization autoclaves, and particularly smaller compact autoclaves.

Another object of the invention is the provision of a cassette tray formed from a single sheet of material such as stainless steel and the provision of an instrument retainer for the cassette tray also formed of single sheet of material such as stainless steel or other resilient material.

Still another object of the invention is the provision of a cassette for medical and dental instruments which has enclosed end portions which protect a user from injury and infection by limiting contact between a user and the sharp tips of the instruments.

Another object of the invention is the provision of a cassette which positively and resiliently retains one or more instruments in place to prevent accidental dulling of sharps by loose jostling of the instruments.

Another object of the invention is the provision of a medical and dental instrument cassette which can be opened and closed with one hand with a simple one-handed pinch and lift movement.

These and other objects are met by the present invention which is directed to a compact cassette for holding medical, dental and other instruments. The cassette includes a tray portion and a retainer portion which together are adapted to fit most compact autoclave bags and particularly those self-sealing commercially available bags dimensioned 5¼ inches by 10 inches.

The cassette is formed with specially shaped tapered and rounded ends which facilitate insertion of the cassette into a compact autoclave bag. The bag is designed to be torn open to remove the cassette after autoclaving. Each end of the cassette is tapered in the manner of a compound wedge, that is, both horizontally and vertically to form a pair of necked-down leading and trailing edges which can easily slide into and out of an autoclave bag. A retainer, having two rows of spring fingers, can be easily inserted into and removed from the cassette tray with one hand. A snap-fit connection is provided for securing the retainer on the cassette tray.

The leading and trailing ends of the cassette tray are partially covered or enclosed with an overhanging wall to cover the sharp tips of instruments and thereby protect a user from punctures, cuts, injury and infection. The entire assembly may be constructed from stainless steel to provide long life.

The cassette can be placed chair-side during dental procedures, and thereafter covered by its retainer using a one hand operation and then taken to an ultrasonic cleaner. After ultrasonic cleaning, the cassette, along with its securely retained instruments, can be easily and safely fitted within an autoclave bag and placed in a compact or standard size autoclave for high temperature sterilization. After autoclaving, the instruments may be kept in a sterilized condition until removal from the autoclave bag and again placed chair-side for use by a dentist, oral surgeon or other medical practitioner.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings:

FIG. 1 is a top plan fragmental view of a cassette base or tray constructed in accordance with the invention and showing in detail over one half of the cassette base which is symmetrical about its center line;

FIG. 2 is a left side elevation view, in fragment, of the cassette base of FIG. 1;

FIG. 3 is a view in section taken along section line 3—3 of FIG. 1;

FIG. 6 is an end elevation view of FIG. 5;

FIG. 7 is a top plan view of FIG. 6;

FIG. 8 is a bottom view of FIG. 7 and

DETAILED DESCRIPTION OF THE PREFERRED EMBODIMENTS

Figure 4:
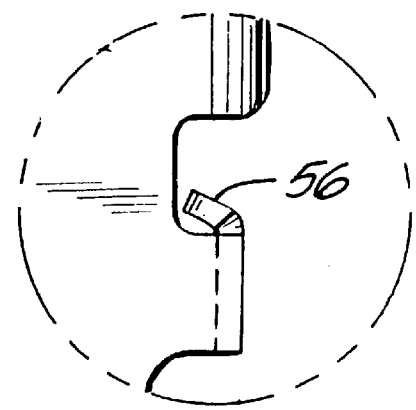
FIG. 4 is an enlarged view in fragment of area 4 of FIG. 2.

The present invention will now be described in conjunction with the drawings, beginning with FIG. 1 which shows the base or tray portion 10 of a cassette for holding instruments such as medical and dental instruments and the like. Base 10 is shown as formed from a single sheet of material. For example, a sheet of 0.030 inch thick ¼ hard series stainless steel has been found to function well. An electropolish may be applied to provide an attractive finish to the base.

Base 10 is provided with a pair of parallel, longitudinally extending, upstanding side walls 12 formed perpendicular to base floor 14. Each side wall 12 has a pair of transversely inwardly extending and longitudinally tapered end portions 16. The opposed end portions 16 at each end of the base 10 taper and converge toward one another into an end wall 18 having a width less than the width of the central portion of the base.

As seen in FIG. 2, end wall 18 has a generally V-shaped side profile defined in part by a lower wall portion 20 extending upwardly and longitudinally outwardly from floor 14 into a rounded leading edge or nose portion 22. End wall 18 further includes an upper wall portion 24 which extends upwardly and longitudinally inwardly back toward the center portion of floor 14 and terminates in a pair of spaced apart downturned lips 26. The overhanging upper wall portion 24 and lips 26 provide a protective cover or shield which can extend over the sharp ends of medical, dental or other instruments placed in and carried by base 10.

A small somewhat V-shaped gap or slot 28 is formed between the end portions 16 of each sidewall 12 and the respective side edge 30 of each end wall 18. Slot 28 is optional and while it facilitates manufacture of the base 10, it also allows for the passage of cleaning fluid into and out of the interior of the base or tray near the sharp ends of the instruments held in the base 10. An arcuate recess 32 is formed between lips 26 along the central portion of the upper portion 24 of end wall 18 to facilitate access to and viewing of instruments carried by the tray 10 and to allow the insertion of long instruments into the tray.

Additional flow and drain passages for cleaning fluid are shown in FIG. 1 in the form of a series of longitudinally-extending transversely-spaced parallel slots 34 which are cut or punched through floor 14. A large, generally rectangular window 36 cut or punched through floor 14 provides an even greater opening for the passage of cleaning fluid.

A serrated instrument support rack 38 is formed on the front or outer edge 40 of each window 36. Each rack 38 is formed from the window material punched and stamped from floor 14. Rack 38 includes an upstanding wall 42, as shown in FIG. 3, having an upper edge 44 formed with a series of transversely extending slots, grooves or notches 46. Notches 46 provide secure seating for the placement of instruments which extend between and over each wall 42. The notches 42 also locate the instruments in the tray so that the fingers of the retainer will fall directly on top of them as described below.

As further seen in FIG. 2, the longitudinal end portions 16 of each side wall 12 extend upwardly to an elevated edge 48 for the purpose of providing protection to a user against accidental injury from any sharp instruments, the tips of which lie behind and between end portions 16. Edge 48 drops downwardly along an arcuate edge portion 50 to a lower wall portion 52. Lower wall portion 52 facilitates access to the instruments held within notches 46.

A pair of guides 54 is formed along the central top portion of each side wall 12 adjacent the inner edge 55 of each window 36. As seen in FIG. 4, each guide 54 includes a bent tab 56 which ramps downwardly toward floor 14 in the direction of the centerline 58 of base 10. The tabs 56 tend to act as downward sliding centering guide surfaces for the installation of the retainer or cover discussed below. Each pair of tabs 56 on each side wall 12 is spaced equidistantly and symmetrically about centerline 58 with the broken away half of base 10 being a mirror image of the half shown up to centerline 58.

Each side wall 12 further includes a central transversely outwardly flared rim portion 60 which provides increased strength and rigidity to the base 10. The flared rim 60 also helps to funnel, shoehorn or guide the cover into the base as discussed below.

A socket in the form of aperture 62 is formed in the center of each side wall 12. Aperture 62 is formed with a somewhat rectangular shape having an upwardly and inwardly arched upper edge 64 for receiving and holding a retainer formed on a cover latch retainer clamp as discussed below. As further seen in FIG. 1, the upper edge 64 of rim 60 is pushed inwardly to form a catch or latch portion 66.

Figure 5:
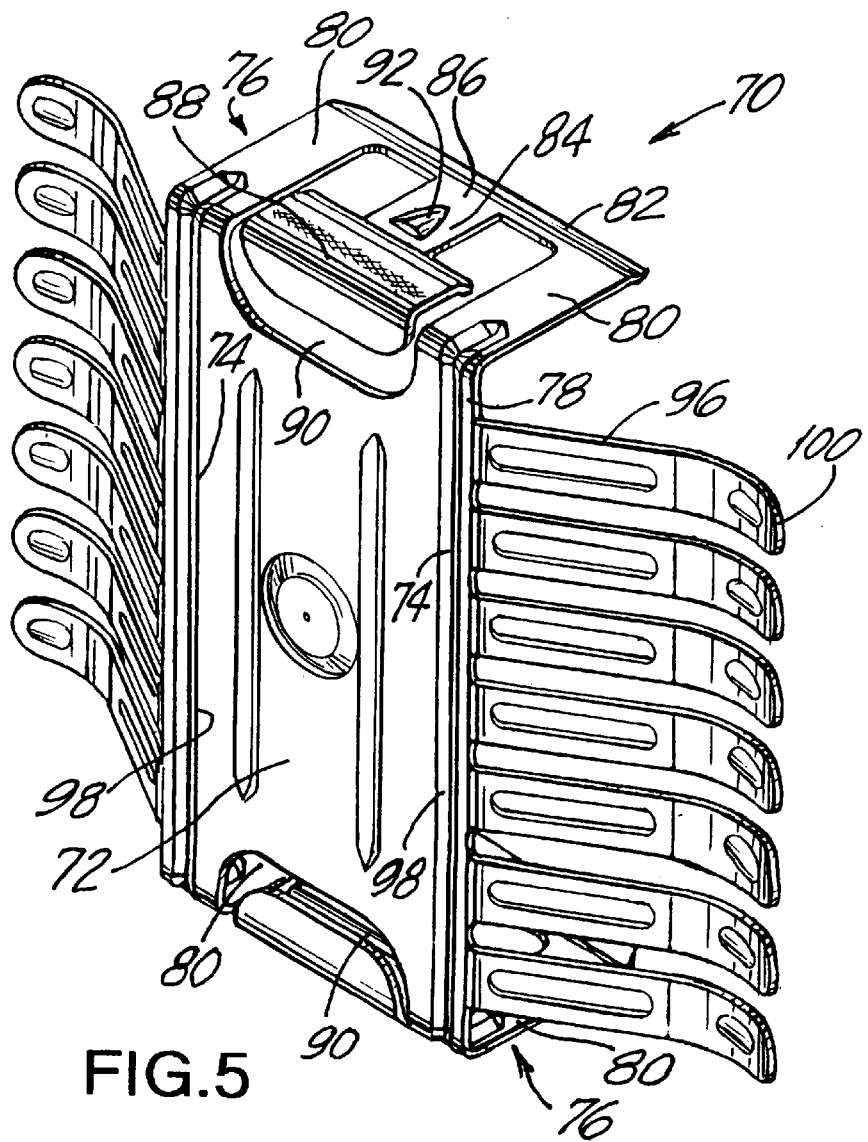
FIG. 5 is a perspective view of a retainer for use with the cassette base of FIG. 1.

Turning now to FIG. 5, a cover latch or retainer 70 is formed as a unitary one-piece stamped part from a sheet of, for example, 0.025 inch thick ½ hard 300 series stainless steel. Retainer 70 may be electropolished to provide an attractive protective finish. The retainer 70 may be formed of other resilient heat resistant materials such as high temperature plastic material.

Retainer 70 includes a flat central body portion or roof 72 having one or more strengthening grooves 74 formed therein. An end wall 76 extends perpendicularly downwardly from each side edge portion 78 of roof 72 to give the central portion of retainer 70 a somewhat inverted U-shaped profile, Each end wall 76 includes a pair of parallel legs 80 interconnected at their outer ends by a cross bar 82.

As seen in FIG. 6, each cross bar 82 is angled or beveled inwardly toward each other to form a pair of wedge-like centering guide surfaces for centering and aligning the retainer 70 between the outwardly flared rims 60 on the top of the central portions of the side walls 12 of base 10. A cantilevered spring latch 84 (FIG. 5) extends upwardly from cross bar 82 midway between each pair of legs 80.

Latch 84 includes a leaf spring base leg 86 and an upper pinch bar 88 extending across the top of base leg 86. Pinch bar 82 has an L-shaped profile extending in part within the plane of end wall 76 and in part within the plane of roof 72.

A recess 90 is formed in each side edge portion 78 of roof 72 and extends down between legs 80 and pinch bar 88 to provide clearance for the swinging transverse pivoting action of latch 84 about its supporting cross bar 82. A wedge-shaped catch or detent 92 (FIG. 6) extends outwardly from each base leg 86. Detent 92 has a flat upper surface 94 which resiliently hooks underneath latch portion 66 of base 10. An upward spring force which drives the surface 94 against the upper edge 64 is provided by the resilient deflection of the leaf spring fingers 96 as noted below.

As seen in FIGS. 6, 7, and 8, a series of leaf spring fingers 96 is cantilevered from the major edges 98 of roof 72 for resiliently retaining dental and other instruments within the notches 46 of rack 38. The free end portion 100 of each finger 96 is aligned directly over each respective notch 46 when the retainer is snapped into the base. A dish-shaped recess 102 (FIG. 6) may be formed on the bottom surface of each free end portion 100 to partially encircle and press downwardly on the handle of each instrument held within a notch 46. In order to decrease the spring force and provide for free fluid flow over the instruments, slots 104 may be formed in each finger 96 as seen in FIGS. 6 and 7.

It can be appreciated that when the retainer 70 is pressed into a snap-fit engagement with the base 10, the ramped guides 54 on side walls 12 engage the outer side edges of the legs 80 on each end wall 76 of the retainer and guide the retainer into proper centered alignment within the sidewalls of the base 10. At the same time, the detents 92 on base legs 86 drag over and wedge themselves against the latch portions 66 along the upper edges 64 of apertures 62 causing the latch 84 to initially pivot inwardly into base 10 and then snap outwardly into aperture 62. This snap fit action locks the retainer 70 to base 10 with the upper surface 94 of each detent 92 pressing upwardly against the upper edges 64 of apertures 62.

As the retainer 70 is locked to base 10, the free end portions 100 of the leaf spring fingers 96 resiliently press down on any instruments held in racks 38. In this manner the instruments are securely retained in racks 38 and are prevented from being jostled about. The reaction force of the spring fingers drives detent 92 upwardly against latch portions 66 as noted above.

Figure 9:
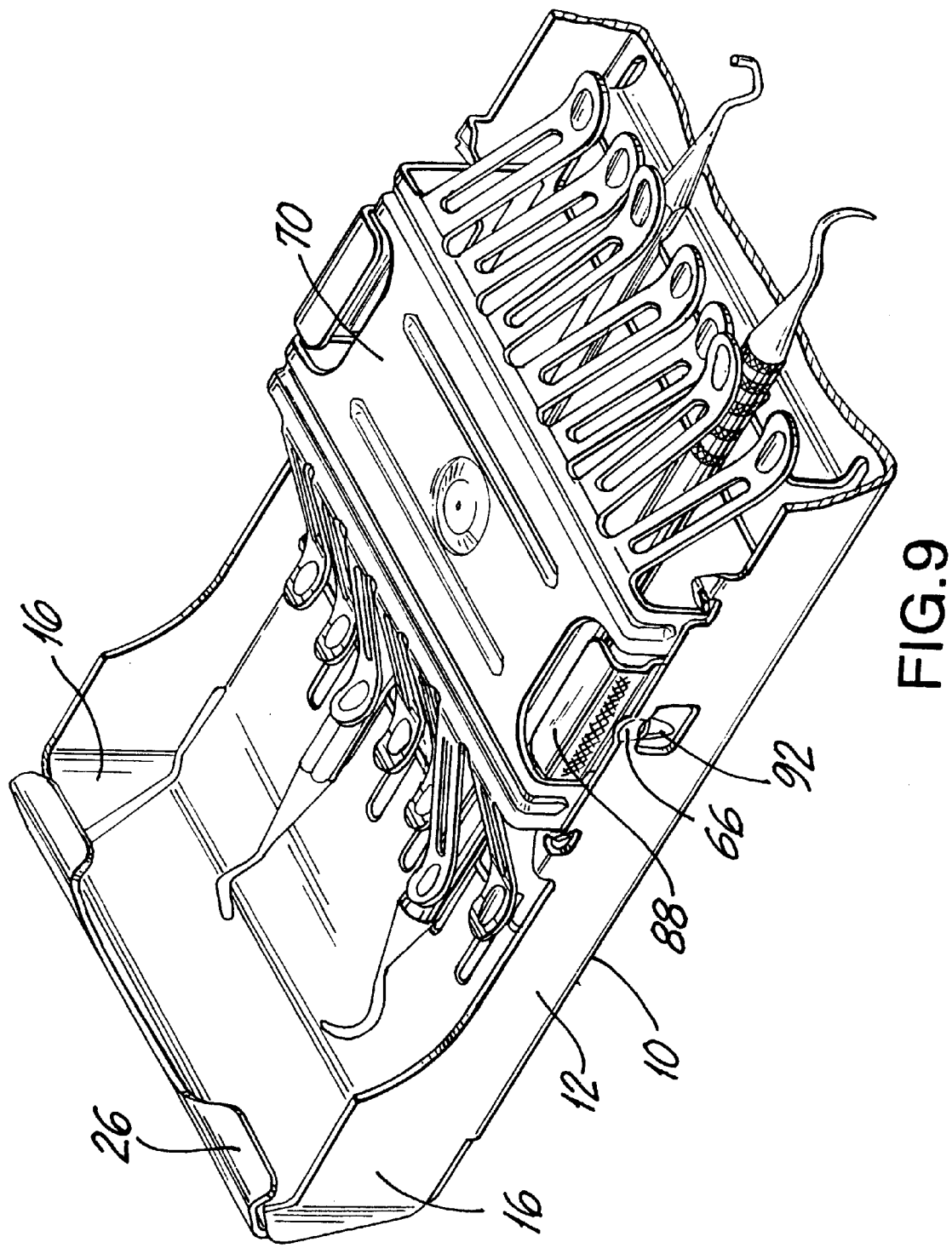
FIG. 9 is a partial perspective view showing a pair of dental instruments clamped between the base and retainer of the present invention.

Should one desire to remove the retainer 70 from base 10 and remove one or more instruments from racks 38, all that is required is a one-handed pinching and lifting movement. That is, as seen in FIG. 9, by pinching the upper pinch bars 88 inwardly toward one another between one's thumb and index finger, and lifting upwardly, the detents 92 swing inwardly beneath edge 64 and latch 66 and allow the retainer 70 to be removed with one hand using a simple lifting motion. The retainer may be easily replaced with a simple downward pushing motion.

There has been disclosed heretofore the best embodiment of the invention presently contemplates However, it is to be understood that the various changes and modifications may be made thereto without departing from the spirit of the invention.

What is claimed is:

1. A compact cassette for holding medical and dental instruments, comprising:
    a base having a central portion, a pair of side walls and a pair of end walls;
    a retainer comprising a central body portion and a plurality of spring fingers projecting outwardly and extending from opposite sides from said central body portion; and
    a spring-biased releasable connection formed between each of said side walls and said retainer,
    wherein each end wall comprises a lower wall portion extending longitudinally outwardly and upwardly and an upper wall portion extending longitudinally inwardly and upwardly so as to overhang said lower wall portion with a gap formed between said side walls and said end walls for passage of cleaning fluid near said instruments held within said compact cassette.

2. The compact cassette of claim 1, wherein each of said side walls has an end portion which tapers inwardly.

3. The compact cassette of claim 1, wherein one of said end walls comprises a rounded nose portion having a width less than the width of said central portion of said base.

4. The compact cassette of claim 1, wherein each of said end walls comprises a rounded end portion having a V-shaped side profile.

5. The compact cassette of claim 1, further comprising a rounded nose portion located between said lower and upper wall portions.

6. The compact cassette of claim 1, further comprising a pair of guides provided on each side wall for guiding said retainer into said base.

7. The compact cassette of claim 1, wherein said connection comprises an aperture formed in each side wall and a pair of spring detents provided on said retainer for releasable engagement within each said aperture.

8. The compact cassette of claim 1, further comprising a pair of notched racks extending upwardly from said base.

9. The compact cassette of claim 1, wherein said releasable connection comprises a pair of cantilevered pinch bars provided on said retainer.

10. The compact cassette of claim 1, wherein said base and said retainer each are formed as a one-piece metal stamping.

11. A dental cassette, comprising:
    a base having a pair of side walls and a pair of end walls, said side walls each having end portions which taper inwardly toward said end walls, said end walls each having a lower portion, an upper portion and a central rounded nose portion for facilitating insertion of said base into an autoclave bag, and wherein said end walls are further provided with a recess to facilitate access to and viewing of instruments held within said dental cassette and to allow the insertion of long instruments into said dental cassette.

12. The cassette of claim 11, wherein each of said end walls comprises an overhanging upper wall portion for partially covering one or more dental instruments.

13. The cassette of claim 11, further comprising a retainer having a central body portion and comprising a pair of resilient spring latches releasably engageable with said base and a plurality of spring fingers projecting outwardly and extending from opposite sides from said central body portion.

14. The cassette of claim 13, wherein said spring fingers further comprise slots for providing fluid communication with instruments to be held in said cassette.

15. The cassette of claim 14, wherein said spring fingers have free ends and dish-shaped recesses formed on said free ends for engagement with instruments to be held in said cassette.

16. The cassette of claim 11, wherein said base comprises a window formed therein and an instrument rack extending upwardly adjacent said window.

* * * * *